United States Patent [19]

Margarit Y Ros et al.

[11] Patent Number: 5,252,478

[45] Date of Patent: Oct. 12, 1993

[54] THERMOSTABLE MUTANTS OF NEUTRAL PROTEASE AND MEANS FOR THEIR PREPARATION

[75] Inventors: Immaculada Margarit Y Ros, San Donato Mil.; Susanna Campagnoli, Codogno; Roberto Gianna, Rome; Salvatore Toma, Milan; Guido Grandi, Segrate, all of Italy

[73] Assignee: Eniricerche S.p.A., Milan, Italy

[21] Appl. No.: 658,908

[22] Filed: Feb. 22, 1991

[30] Foreign Application Priority Data

Feb. 23, 1990 [IT] Italy .................. 19474 A/90

[51] Int. Cl.⁵ .............. C12N 15/00; C12N 15/57; C12N 9/56; C12N 15/75
[52] U.S. Cl. ....................... 435/222; 435/221; 435/69.1; 435/252.31; 435/320.1; 536/23.2
[58] Field of Search ............ 435/220, 221, 222; 536/27, 23.2

[56] References Cited

U.S. PATENT DOCUMENTS

| | | | |
|---|---|---|---|
| 4,914,031 | 4/1990 | Zukowski et al. | 435/222 |
| 4,966,846 | 10/1990 | Deutch et al. | 435/172.3 |
| 4,990,452 | 2/1991 | Bryan et al. | 435/222 |
| 5,021,340 | 6/1991 | Toma et al. | 435/69.1 |
| 5,041,378 | 8/1991 | Drummond et al. | 435/234 |

OTHER PUBLICATIONS

Takagi, M., et al., 1989, FEBS Letters, 254(1,2):43–46.
Imanaka, T., et al., 1986, Nature, 324:695–697.
Pauptit, R. A., et al., Journal of Molecular Biology, 199:525–537.
Kubo, M., et al., 1988, Journal of General Microbiology, 134:1883–1892.
Nishiya, Y., et al., 1990, Journal of Bacteriology, 172(9):4861–4869.
Shimada, H., et al., 1985, Journal of Biotechnology, 2:75–85.
Levy, P. L., et al., 1975, Proceedings, National Academy of Sciences, USA, 72(11):4341–4345.
Toma, S., et al., 1989, *Protein Engineering*, 2(5):359–364.
Pangburn, M. K., et al., 1975, *Eperientia*, (Supplement), 19–29.

*Primary Examiner*—Robert A. Wax
*Assistant Examiner*—William W. Moore
*Attorney, Agent, or Firm*—Sughrue, Mion, Zinn, Macpeak & Seas

[57] ABSTRACT

The mutants of neutral protease (NP) described can retain their enzymatic activities at temperatures at which wild-type neutral protease becomes inactive, the mutants being characterised in that the Gly 189 and/or Gly 147 residues of the aminoacid sequence of NP are replaced by different residues selected from the natural aminoacids.

Mutagenised genes of neutral protease which code for the mutants, recombinant plasmids containing the genes, and strains of Bacillus transformed by the plasmids are also described. The mutants of neutral protease having the characteristics described above are particularly useful in the food sector.

6 Claims, 6 Drawing Sheets

THERMOSTABLE MUTANTS OF NEUTRAL PROTEASE AND MEANS FOR THEIR PREPARATION

DESCRIPTION

The present invention relates to mutants of neutral protease which retain their enzymatic activities at temperatures at which wild-type neutral protease becomes inactive, and means and methods for their preparation and their use in the food sector.

In particular, the present invention relates to mutants of neutral protease characterised in that the Gly 189 and/or Gly 147 residues of the aminoacid sequence of neutral protease are replaced by different residues selected from the natural aminoacids.

Enzymes are the most abundant class of proteins present in nature. Each enzyme generally catalyses a different kind of chemical reaction and its function is highly specific. An enzyme molecule contains an active site to which a specific substrate binds during the catalytic reaction.

Living organisms use many enzymes to carry out a multitude of catalytic reactions. Up to now, however, no more than 2000 enzymes have been characterised in detail, and of these only a few are available commercially.

The factors limiting the industrial use of an enzyme are not only the high costs of production and purification but also the fact that the characteristics of enzymes present in nature (wild-type enzymes), such as their resistance to oxidation, their thermal stability, their pH and the like, are not necessarily optimised when they are used in environments different from their original environments. In fact, industry generally requires particularly "robust" enzymes, since the substrates and/or products desired, like the reaction conditions, are often different from those occurring physiologically.

It may therefore be desirable to alter one or more of the natural characteristics of an enzyme for a specific use or for its use in a specific environment.

The development of genetic engineering techniques has enabled a protein to be modified at one or more sites of its primary structure by intervention at the DNA level, so as to obtain a product with characteristics more suitable for the process of interest.

Bacterial proteases are enzymes currently used in industrial processes both in the food sector and the detergents sector. Most of the proteases used are produced from strains of Bacillus and are classified into two large categories: serinic proteases, which are used mainly as additives in the detergents industry, and neutral proteases, which are used in the food sector and, in particular, in the brewing industry.

From technical and patent literature, many method are known for the preparation by genetic engineering of serinic proteases with high resistance to oxidising agents (Estell, D.A. et al., (1985), J. Biol. Chem: 260, 6518-21), to temperature (Imanaka, T. et al., (1986), Nature, 324, 695-697) and to denaturing by detergents (U.S. Pat. No. 4,760,025).

As regards neutral protease, the literature describes a method for improving the thermal stability of neutral protease produced from *B.stearothermophilus* by the replacement of one or more aminoacid residues in certain positions.

The availability of these techniques does not, however, suggest the aminoacid replacement or replacements which should be carried out to achieve the desired results.

Moreover, the mutations introduced into the enzymatic proteins in order to alter one or more characteristics often induce an undesired reduction in their enzymatic activity.

It has now been found that it is possible to improve the thermostability of neutral protease without altering its enzymatic activity by the replacement of one or more residues in well-defined sites of the aminoacid sequence of NP.

An object of the present invention is therefore to provide mutants of neutral protease which retain their enzymatic activities at temperatures at which wild-type neutral protease becomes inactive.

A further object of the present invention is a mutagenised gene which codes for a mutant of neutral protease which retains its enzymatic activity at a temperature at which wild-type neutral protease becomes inactive.

A further object of the present invention is a replicable expression vector in Bacillus including the mutagenised gene.

Another object of the present invention is a strain of Bacillus transformed by the vector.

A further object of the present invention is a method for the production of a mutant of neutral protease which retains its enzymatic activity at a temperature at which wild-type neutral protease becomes inactive including the growth, in a suitable culture medium, of a strain of Bacillus transformed by a replicable expression vector including the mutagenised gene which codes for the mutant, and the separation and purification from the culture medium of the mutated enzyme thus obtained.

A further object of the present invention is the use of the mutants of neutral protease in the food sector.

Further objects of the present invention will become clear from a reading of the description and examples which follow.

In particular, mutants of neutral protease according to the present invention are characterised in that the glycine (Gly) aminoacid residues in positions 189 and/or 147 of the aminoacid sequence of neutral protease are replaced by a different residue selected from the natural aminoacids.

According to the present invention, mutants of neutral protease in which the Gly aminoacid residue and/or residues are replaced by the alanine (Ala) aminoacid residue are preferred.

According to the present invention, the mutant of neutral protease including the double 147/189 Gly → Ala replacement is particularly preferred.

According to the present invention, the numbering system adopted is that of thermolysin, an enzyme which is produced by *B.thermoproteoliticus* and is very similar to neutral protease, by the alignment of their aminoacid sequences (Toma, S. et al., (1989), Pro. Eng., 12: 359-364).

Mutants of neutral protease according to the present invention are prepared by a method comprising:
 a) the introduction of one or more mutations at specific sites of the gene which codes for neutral protease with the use of the in vitro mutagenesis technique;
 b) the cloning of the mutagenised gene produced in step a) in a cloning vector with expression and secretion in Bacillus;

c) the transformation of a strain of Bacillus by the recombinant vector obtained in step b);
d) the growth, in a suitable culture medium, of the strain of Bacillus transformed as in step c), and finally
e) the separation and purification from the culture medium of the mutant of neutral protease produced.

In step a) of the method of the present invention, the mutations may be introduced in well-defined sites of the gene with the use of one of the known in vitro mutagenesis techniques. Of the various techniques which produce desired modifications in a DNA sequence, the most widely used are those which use single-helix synthetic oligonucleotides.

According to one embodiment of the present invention, the method described by Zoller, M.J. and Smith, M (1982), Nucl. Acid. Res., 10, 6487-6500) is used and comprises:

1) the insertion of the gene of neutral protease or part thereof (the target sequence) in an M13 phage or in a plasmid derived therefrom and the preparation thereof in the form of a single strand which can be used as a "template" for synthesising the mutant;
2) the synthesis of an oligonucleotide complementary to the sequence to be mutagenised except for an internal portion which causes the mutation;
3) the "annealing" of the synthetic oligonucleotide to the "template". This will act as a "primer" for the synthesis of the second modified strand;
4) the reconstitution of the circular double-helix structure, of which one strand is the parent strand and the other carries the desired mutation, by a polymerisation and ligation step in vitro;
5) the use of the double-helix form to transform host cells which have been made competent, to produce a population of mutant and wild-type clones;
6) the selection of the mutant clones by hybridisation with specific oligonucleotides, the sequencing of the clones produced, or restriction analysis.

As far as the gene of neutral protease to be mutagenised is concerned, this can be isolated from various species of Bacillus.

According to a preferred embodiment of the present invention, the gene of neutral protease and the sequences which regulate its expression and secretion are isolated from a strain of *B.subtilis* which is an overproducer of neutral protease, and are cloned in the plasmid pSM 127. This plasmid, which is deposited in the Agricultural Research Service Culture Collection as *B.subtilis* SMS 108 NRRL B-15900, includes the replicon of *B.subtilis* and the gene which codes for resistance to kanamycin as a marker for the selection of the transformants.

According to the present invention, the Bam HI-Hind III fragment of about 1550 base pairs including the nucleotide sequence which codes for mature neutral protease and part of the pro region of the gene of neutral protease is isolated from the plasmid pSM 127 NRRL B-15900 by digestion with Bam HI and Hind III restriction enzymes.

The fragment is then inserted in the M13 mp8 phage, which is digested beforehand with the restriction enzymes mentioned above, by ligation in ligation mixture according to known techniques.

The mixture is used to transform *Escherichia coli* (*E.coli*) cells made competent as described by Dagert, M and Ehrlich (1979), (Gene, 6: 23) and the transformants are then selected on a suitable culture medium. After the single-helix strand has been prepared from one of the positive plates, it is used as a template for introducing the desired mutations.

One of the methods known to an expert in the art can be used for this purpose, for example, the method described by Zoller and Smith (1983), (Methods in Enzymol., 100: 468-500).

In particular, in order to insert the Gly → Ala substitutions in positions 189 and 147 respectively, the following synthetic oligonucleotides are used:

(SEQ. ID. No. 1)
1) G A A G A C T G G <u>G A T A T C G C A</u> G A A G A C
                    <u>Eco RV</u>   Ala
A T T A C G G T C (SEQ. ID. No. 2)
2) C A T G A A A T G A C <u>G C A T G C A</u> G T C A C C
                     <u>Sph I</u>   Ala
C A A G A A A C A These oligonucleotides are synthesised by known methods with the use of an automatic synthesiser.

The single helix is then "annealed" to the synthetic oligonucleotide which will act as a "primer" for the synthesis of the second modified strand.

After the desired mutations have been effected, the double-helix circular structure of the target sequence, of which the first strand is the parent strand and the other strand carries the desired mutation, is reconstituted by a polymerisation and ligation step in vitro.

According to the present invention, the genes mutagenised as described above can then be inserted in a cloning vector with expression and secretion in Bacillus, the gene being positioned correctly under the control of sequences which regulate its expression and secretion in the host strain.

Vectors suitable for the purpose may be selected from plasmids available commercially or from authorised collection centres. Preferably, the plasmid pSM 127 NRRL B-15900 is used.

In practice, the plasmid is digested with Bam HI and Hind III restriction enzymes and the 6131 base-pair plasmid DNA fragment containing the sequences for regulating the expression and secretion of neutral protease is ligated to the 1550 base-pair fragment containing the mutagenised gene by techniques known in the recombinant DNA field.

The resulting recombinant plasmids are then inserted in a host microorganism selected from the *B.subtilis* group.

According to a preferred embodiment of the present invention, the strain *B.subtilis* SMS 108 deposited in the Agricultural Research Service Cultural Collection as NRRL B-15898 is used; this strain does not express wild-type neutral protease due to the presence of mutations which inactivate the chromosomal gene which codes for neutral protease.

In step d) of the method of the present invention, the strains are grown in a suitable medium containing sources of carbon, nitrogen and mineral salts at a temperature of about 37° C. for the period of time necessary to produce the desired product.

Typically, the strains of *B.subtilis* SMS 108 transformed by the plasmid pSM 127 (the control) and by those containing the mutagenised neutral protease gene are grown in Veal Infusion medium (DIFCO) at a temperature of 37° C. for 16 hours.

Upon electrophoretic analysis on polyacrylamide gels (Laemmli, U.K., (Nature, 227, 680–685, 1970), the supernatant liquids obtained after the culture has been centrifuged show a neutral protease content of from 50 to 100 mg/l which represents more than 80% of the total proteins secreted.

Mutants according to the present invention can be purified with the use of one or more conventional chromatographic techniques.

According to the present invention, the method described in Example 3 below produces mutants with purities greater than 95%.

The enzymatic activity of the mutants according to the present invention was determined by the monitoring of the hydrolysis both of the specific substrate casein, according to the method described by Kunitz, M., (1974), J. Gen. Physiol., 30, 291, and of specific synthetic peptides.

The results obtained showed improved enzymatic activity comparable to that of wild-type neutral protease for the single 189 mutant and for the double 147/189 mutant but the enzymatic activity of the single 147 mutant was reduced (by approximately half for casein).

Furthermore, thermal inactivation studies carried out at different temperatures showed that the three mutants had greater thermal stability than wild-type neutral protease.

In fact, if the mutants are kept at a preincubation temperature for a period of 30 minutes, their enzymatic activities are halved by temperature increases of 4° C. for the 147 mutant, 3° C. for the 189 mutant and 7° C. for the double mutant 147/189.

Moreover, a study of the kinetics of their thermal inactivation at different temperatures (55° C., 58° C. and 61° C.) showed an average life, where this term means the time necessary to halve the enzymatic activity, about seven times as long as that of wild-type neutral protease for the double mutant 147/189, 3 times for the 147 mutant and about twice for the 189 mutant.

In summary, the single 147 mutation induces an increase in thermal stability but a decrease in enzymatic activity; the single 189 mutation increases thermal stability although to a lesser extent than the 147 mutation, with improved catalytic efficiency; the double mutation 147/189 induces markedly greater thermal stability than is achieved by the single mutations (an additive effect) and re-establishes the enzymatic activity altered by the single 147 mutation.

Although the invention is described with reference to the production of thermostable mutants of the neutral protease of B.subtilis, clearly it can also be applied to the modfication of homologous neutral protease obtained from other microorganisms and, in particular, from other strains of Bacillus.

According to the present invention, the plasmids pSM 375 and pSM 376 containing the single Gly 189 mutation and the double Gly 147/189 mutation respectively have been deposited at the Centraalbureau Voor Schimmelcultures (CBS) as B.subtilis 108 (pSM 375) CBS 640.89 and B.subtilis 108 (pSM 376) CBS 641.89.

BRIEF DESCRIPTION OF THE DRAWINGS

The glycine in position 147 is located in the alpha helix of the molecule which forms part of the active site of the enzyme, whilst the glycine in position 189 is in a structural loop positioned in front of the site itself.

MCS=the multiple cloning site; SS=single-helix DNA of M13 mp8; LS, PRO and MAT indicate the leader sequence or secretion signal sequence, the pro region and the mature region of neutral protease, respectively. The broken arrow shows the action of the Klenow fragment of Pol I (Pol K) DNA.

The following experimental examples are intended further to illustrate the present invention and are not intended to be limiting thereof.

EXAMPLE 1

The construction of thermostable mutants of neutral protease

A) The cloning of the Bam HI-Hind III fragment of the gene of the neutral protease of B.subtilis in the phage M13 mp8

The plasmid pSM 127 (3ug) was digested with 5 units of Bam HI and Hind III restriction enzymes (Boehringer) at 37° C. for 1 hour. After the enzymatic reaction had been stopped at 65° C. for 10 minutes, the digestion mixture was loaded onto 0.8% agarose gel and run at 100 volts for 2 hours. The 1550 base-pair (bp) Bam HI-Hind III band including the sequence which codes for the mature portion of neutral protease and part of the pro region was then electroeluted with the use of I.B.I apparatus model U.E.A. according to the manufacturer's instructions.

500 ng of the DNA fragment corresponding to that band were ligated to 750 ng of the vector M13 mp8 digested beforehand with Bam HI and Hind III restriction enzymes (5 U). The ligation reaction was carried out in 50 ul of ligation mixture containing 66 mM Tris-HCl, pH 7.6, 1 mM ATP, 10 mM $MgCl_2$, and 10 mM dithiothreitol (DTT) in the presence of 4 U of T4 DNA ligase at 14° C. for one night.

The ligation mixture was then used to transform E.-coli JM 101 cells (BRL) made competent with 50 mM $CaCl_2$ (Dagert, M. and Ehrlich, (1979), Gene, 6: 23).

The transformants were then selected on YT agar plates (8g/l Bacto triptone (DIFCO), 5 g/l Bacto Yeast Extract (DIFCO), 5 g/l NaCl) containing 40 ug/ml of X-Gal (5-bromo-4-chloro-3-indolyl-D-galactopiranoside) and 125 µg/ml IPTG (isopropyl-beta-D-thiogalactopiranoside).

The method described above produced many positive recombinant plates (white) which were easily distinguishable from the non-recombinant plates (blue).

In order to check that the Bam HI-Hind III fragment had been inserted in the desired orientation, the double-helix phage DA (the replicative form or RF) was isolated from some positive plates and digested with Bgl II enzyme (Boehringer).

The single-helix (SS) phage DNA was then prepared from one of the positive plates which showed the correct insertion for use as a template in the site-specific mutagenesis step.

B) Site-specific mutagenesis

The method described by Zoller and Smith (Methods in Enzymol., 100, 468–500, 1983) was used with the use of the following oligonucleotides for the Gly → Ala mutations in positions 189 and 147 respectively:

(SEQ. ID. No. 1)
1) G A A G A C T G G <u>G A T A T C G C A</u> G A A G A C
   <u>Eco RV</u>      Ala
A T T A C G G T C (SEQ. ID. No. 2)
2) C A T G A A A T G A C <u>G C A T G C A</u> G T C A C C
   <u>Sph I</u>      Ala
C A A G A A A C A

These oligonucleotides were synthesised by known methods with the use of a One Plus DNA Synthesizer (Beckman), a restriction site being created upstream of the mutation site to enable the mutated clones to be selected easily by restriction analysis of their DNA. The double mutant was produced with the use of the single-helix DNA containing the Gly → Ala mutation in position 189 as a template and the oligonucleotide No. 2 as the primer.

Figure 1:
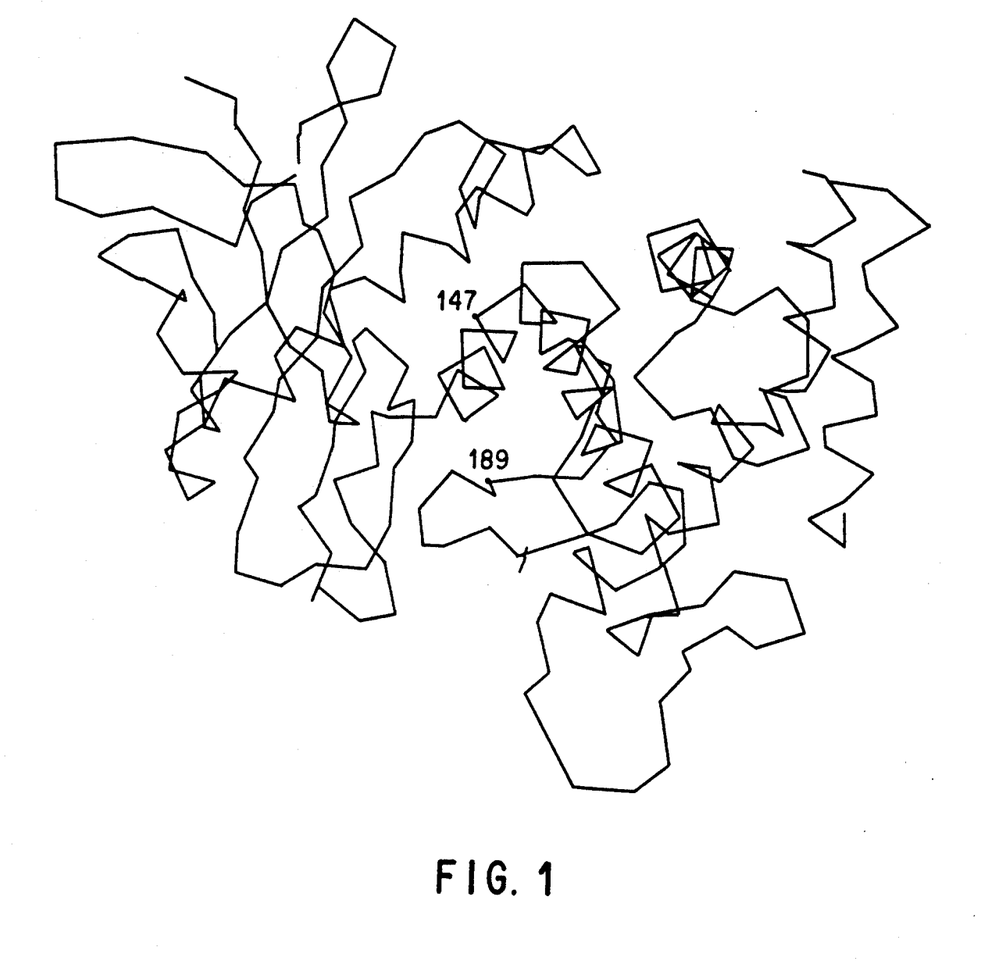
FIG. 1: shows the three-dimensional structure of neutral protease deduced by comparison with the known structure of thermolysin (Signor et al. Eur. Biochem. (1990) in course of printing) and shows the positions of the aminoacids 147 and 189.
Figure 2:
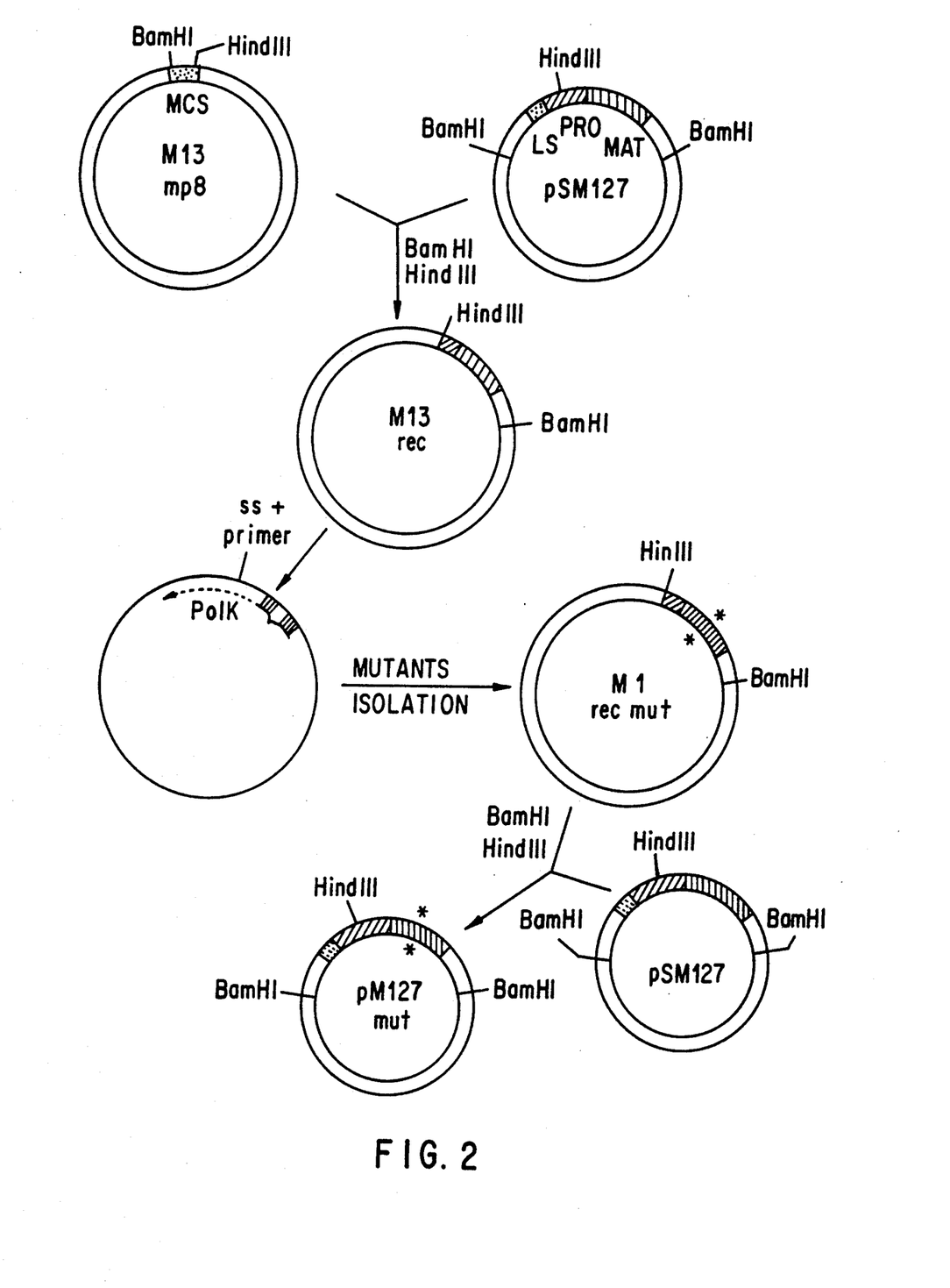
FIG. 2: is a schematic representation of the site-directed mutagenesis of the gene which codes for the neutral protease of B.subtilis. The asterisks indicate the codon which has been modified.

FIG. 2 is a diagram showing the method followed for the mutagenesis.

In practice, 44 picomoles (pmoles) of the oligonucleotide used as the primer were phosphorylated in 30 ul of 100 mM Tris-HCl, pH, 8.00, 10 mM MgCl$_2$, 5 mM DTT and 0.1 mM ATP. The phosphorylation reaction was carried out at 37° C. for 45 minutes in the presence of 4.5 U of polynucleotide kinase (Boehringer). For the "annealing" and polymerisation reactions, the SS phage DNA (the template) and the primer, used in a molar ratio of 1:30, were incubated first at 55° C. for 5 minutes and then at 23° C. for another 5 minutes and finally at 15° C. for 16 hours in the presence of 0.5 mM of the deoxynucleotides (dATP, dGTP, dCTP and dTTP), 2.5 Units of Klenow (Boehringer) and 2 Units of T4 DNA ligase in a final volume of 20 ul.

In order to isolate the covalently-closed double-helix DNA (cccDNA), the reaction mixture was loaded onto a sucrose gradient of from 5 to 20% in 1M NaCl, 0.2 N NaOH, 2 mM EDTA and ultracentrifuged at 37,000 revolutions (rpm) for 4 hours with the use of an SW40 rotor (Beckman).

The fractions corresponding to the cccDNA were collected and used to transform competent E.coli JM 101 cells. The transformants were then selected on YT medium to which X-Gal and IPTG had been added as described above.

In order to identify the positive plates containing the Gly → Ala mutations introduced in positions 189 and/or 147, the double-helix phage DNA extracted from the plates was digested with the enzymes Eco RV and Sph I respectively.

Moreover, in order to confirm the presence of the mutations introduced, the single-helix DNAs prepared from the positive clones as described above were sequenced by Sanger's method (Sanger, F. and Coulson, A.R., (1975), J. mol. Biol., 94: 441–443) with the use of the oligonucleotide GGTTCATTCTTCTCTCCG as the primer (SEQ. ID. No. 3).

EXAMPLE 2

The cloning of the mutated Bam HI-Hind III fragment in the plasmid pSM 127

1.6 ug of the mutagenised double-helix phage DNA were digested with Bam HI and Hind III restriction enzymes (5 U) at 37° C. for 1 hour.

After the enzymatic reaction had been stopped at 65° C. for 10 minutes, a portion of the digestion mixture was loaded onto 0.8% agarose gel and run at 100 volts for 2 hours in order to check that the digestion was complete.

The remaining digestion mixtures were then used to ligate 500 ng of the plasmid pSM 127 previously digested with Bam HI and Hind III restriction enzymes (5 U). The reaction was carried out in 20 ul of ligation mixture containing 66 mM Tris-HCl, pH 7.6, 1 mM ATP, 10 mM MgCl$_2$, and 10 mM dithiothreitol (DTT) in the presence of 1 U of T4 DNA ligase at 14° C. for one night.

The ligation mixtures were used to transform B.subtilis SMS 108 NRRL B-15898 cells (npr$^-$, rec$^-$) made competent as described by Dubnau and Contente (1979), (Mol. Gen. Genet., 167, 251–258).

The transformants were then selected on plates of agarised VY medium (0.8% Bacto triptone, 0.5% Yeast Extract, 0.5% NaCl) containing 1% casein and 5 ug/ml of kanamycin.

The plasmid DNAs isolated from one of the positive clones (kanamycin-resistant) thus obtained were then tested by analysis with Eco RV and/or Sph I restriction enzymes to check the correct insertion of the mutagenised fragments in the plasmid pSM 127.

The plasmids containing the single 147 and 189 mutations and the double 147/189 mutation were designated pSM 374, pSM 375 and pSM 376 respectively.

EXAMPLE 3

The characterisation of the mutated neutral proteases

A) The expression and secretion of the mutated proteases

Strains of B.subtilis SMS 108 containing the plasmids pSM 374 (B.subtilis SMS 263), pSM 75 (B.subtilis SMS 261), pSM 376 (B.subtilis SMS 262, and B.subtilis (pSM 127) NRRL B-15900 (the control), respectively, were grown for 16 hours at 37° C. in 3 l of a medium having the following composition: 2.5% veal infusion broth (DIFCO), 0.5% yeast extract, 5 ug/ml kanamycin.

The cultures were then centrifuged at 5000 rpm for 10 minutes (Beckman SJ14 rotor) and portions of the acellular supernatant liquids were analysed by electrophoresis on polyacrylamide gel (Laemmli, U.K., (1970), Nature, 227, 680–685) to determine their protein content.

Concentrations of 50-100 mgl were obtained, which represents more than 80% of the total extracellular proteins.

B) Purification

The neutral proteases obtained as described in step A) were then purified by the following procedure at 4° C.

a) Precipitation with ammonium sulphate

The proteins were precipitated by the addition to the acellular supernatant liquid, which was kept under gentle agitation, of ammonium sulphate to 80% saturation over a period of about 18 hours. After the suspension had been centrifuged at 5000 rpm for 10 minutes, the proteinaceous precipitate was separated, resuspended in 30 ml of 25 mM Tris-HCl, pH 7,5, 2.5 mM Ca-acetate buffer and dialysed extensively against the same buffer.

b) Anion-Exchange Chromatography on DEAE-Sephadex ®A25.

The solution obtained as described in step a) was loaded into a chromatography column (2.6×40 cm) (diameter×height) containing 200 ml of DEAE-Sephadex ®A25 and equilibrated with 25 mM Tris-HCl, pH 7.5, 2.5 mM Ca-Acetate buffer. The flow rate was 30 ml/hour. Elution was effected with the use of the same buffer as for the equilibration. The fractions (5 ml each) which showed enzymatic activity, determined as described in Example 3 below, were recovered and recombined.

Under these conditions, almost all the neutral protease was eluted from the column.

c) Gel filtration on Sephadex ®G-100

The enzymatically active fractions from step b) were then concentrated on DIAFLO ultrafilters (AMICON YM10) and further purified by gel filtration on 200 ml of Sephadex ®G-100 in a 1.6×100 cm column equilibrated in 25 mM Tris-HCl pH 7.5, 2.5 mM Ca-acetate buffer with elution with the same buffer.

The flow rate was 6 ml/hour and fractions, each of 3 ml, were collected.

Calibration was carried out beforehand with standards of various molecular weights under the same conditions as described above.

During the elution, neutral protease activity was found in the region relating to 31 Kd which, allowing for experimental error, corresponds to the predicted molecular weight of the aminoacid sequence of NP (Toma, S. et al., (1986), J. Bacteriol., 167: 740-743).

The enzymatically active fractions were recovered and recombined.

d) Gly-D-Phe affinity chromatography

The method of Walsh, K.A. et al., (1974) Methods Enzymol., 34: 435-440, which is based on the high affinity of the competitive inhibitor Z-Gly-D-Phe (N-carbobenzoxy-glycyl-D-phenylalanine) for metallo-proteinases, was used.

The maximum affinity for neutral protease was found at pH 5, whilst at pH 9 it was no longer retained by the inhibitor.

The proteinaceous fractions from step c) were loaded into a chromatographic column (2.6×14 cm) of Sepharose ®4B bound covalently to the Gly-D-Phe group and equilibrated with 100 mM NaCl, 5 mM Ca-acetate, pH 5 buffer. In these conditions, the wild-type neutral protease and the 189 mutant were wholly retained in the column, the 147/189 mutant was only partially retained, whilst the 147 mutant was not retained.

The proteins were eluted from the column with the use of 100 mM Tris-HCl, pH 7.5, 5 mM Ca-acetate buffer.

Electrophoretic analysis on 12.5% polyacrylamide gel (SDS-PAGE) showed that the products obtained had purities of more than 95% (FIG. 3) and the yield was about 25% of the raw material loaded.

EXAMPLE 3

Determination of enzymatic activity on casein

The enzymatic activity of the mutants was determined by the monitoring of the hydrolysis of the casein substrate as described by Kunitz, M., (1947), J. Gen. Physiol., 30, 291.

In practice, a 0.6% solution of casein was prepared in 50 mM Tris-HCl, pH 7.0, 2 mM Ca-acetate buffer. A quantity of enzyme corresponding to 8 ug of purified protein was then added to 5 ml of this solution. The proteinaceous concentration was determined spectrophotometrically (Perkin-Elmer lambda-15 spectrophotometer) as the absorbance value (O.D.) at 280 nm. An O.D. of 13.7 corresponds to a concentration of neutral protease of 1%.

After incubation for 10 minutes at 37° C., 5 ml of 10% trichloroacetic acid (TCA) were added to the solution in order to stop the enzymatic reaction.

The resulting mixture was centrifuged for 10 minutes at 10,000 rpm and the absorbance of the supernatant liquid thus obtained was evaluated spectrophotometrically at 275 nm against a blank constituted by casein which had not been hydrolysed by the enzyme.

An increase in absorbance (O.D.) of 0.2/10 minutes was observed for the wild-type protein and the 189 and 147/189 mutants and of 0.1/10 minutes for the 147 mutant. Both these values fall within the range of linearity of the kinetics.

According to this method, one enzymatic unit is equivalent to the quantity of enzyme which produces an O.D. increase of 0.001/minute which corresponds to the release of 1 umole of tyrosine (Tyr) from the casein substrate. The specific activity was expressed as Units/mg (U/mg) of protein.

The specific activity of the wild-type protein, the single 189 mutant, and the double mutant was 12,425 U/mg whilst that of the 147 mutant was 7,100 U/mg.

Figure 3:
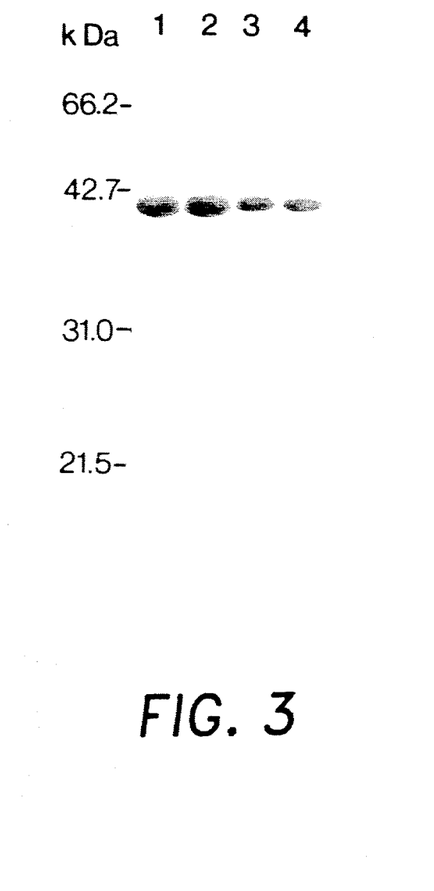
FIG. 3: shows the electrophoretic analysis on 12.5% polyacrylamide gel (SDS-PAGE) of the purified wild-type NP enzyme (track 1), 189 (track 2), 147 (track 3) and 147/189 (track 4).

This latter value is not due to the presence of contaminating proteins, but to an actual decrease in enzymatic activity, the degree of purity in fact being comparable to that obtained for the other proteins (FIG. 3).

EXAMPLE 4

Determination of catalytic efficiency on peptide substrates

The kinetic parameters Km and Kcat of wild-type neutral protease and of the three mutants were determined on Z-Phe-Leu-Ala, Z-Ala-Leu-Ala, Z-Gly-Leu-Ala and Z-Val-Leu-Ala synthetic peptide substrates (Bachem, Bubendorf, CH).

The hydrolysis reactions were carried out at 37° C. in 0.6 ml of a solution containing 25 mM Tris-HCl, pH 7.0, and 2.5 mM calcium acetate, with the use of different concentrations of the substrate (from 0.2 to 20.0 mM) and of the enzyme (from 0.04 to 5 ug/ml).

100 µl portions were withdrawn from the reaction mixtures at various time intervals, and 100 µl of a solution of $H_2O:CH_3CN:H_3PO_4$ in a volumetric ratio of 64:34:1 were added and the mixture centrifuged at 14,000 rpm for 5 minutes.

20 µl of the supernatant liquid thus obtained were then loaded into a VYDAC® 218 TP S415 HPLC column (4.6×150 mm, 10 μm particles) and the hydrolysis products (Z-Phe, Z-Ala, Z-Val and Z-Gly) were separated by isocratic elution at a flow rate of 1.5 ml/minute with the use of solutions A (0.05% $H_3PO_4$, v/v) and B ($H_2O:CH_3CN:H_3PO_4$, 4.95:95.0:0.05 v/v) in ratios which varied according to the substrate used.

The reaction products were measured as their absorbance at 220 nm and quantised by the integration of the elution peaks with the use of the System Gold program (Beckman).

For each of the substrates tested, Table I shows the quantity of solution B used in the elution as a percentage of the quantity of solution A, the concentration of the enzyme (μg/ml) and of the peptide (mM) used in the reaction, the time intervals between the withdrawals, and the retention time of each substrate and product.

Initial velocities (vi) and maximum velocities (Vmax) Km and Kcat were then found for each of the substrates with the use of the Michaelis-Manten equation $$v = \frac{(E)_o (S) Kcat}{Km + (S)}$$

Table II shows the values of Km, Kcat, and the catalytic efficiency (expressed as the Kcat/Km ratio) for each of the mutants and substrates studied.

The results given in this table indicate a decrease in catalytic efficiency for the 147 mutant (confirming the data obtained on casein), an increase in catalytic efficiency for the 189 mutant (from 7 to 14 times for 3 of the substrates) attributable in particular to a high affinity for the substrate (the Km values were lower than for the wild type), and catalytic efficiency values comparable to those of wild-type neutral protease for the double 147/189 mutant.

and of the single mutants (1mg/ml) in 25 mM Tris-HCl, pH 7.5, 2.5 Ca-acetate buffer at various temperatures.

Each sample was inserted in a Durham glass tube and preincubated in a thermostatically-controlled bath equilibrated at the preselected temperature. The samples were prevented from evaporating by the closure of the tubes with parafilm. Portions (50 μl) of each sample were withdrawn at various times, diluted in 5 ml of a buffer solution containing 0.6% casein and tested at 37° C. for 10 minutes as described in Example 4. The measurement at time 0 corresponds to the hydrolysis yield of casein determined before the sample was immersed in the thermostatically-controlled bath.

The graph of the percentage activity remaining against time is linear, suggesting that the inactivation reaction takes place according to first-order kinetics.

Figure 4:
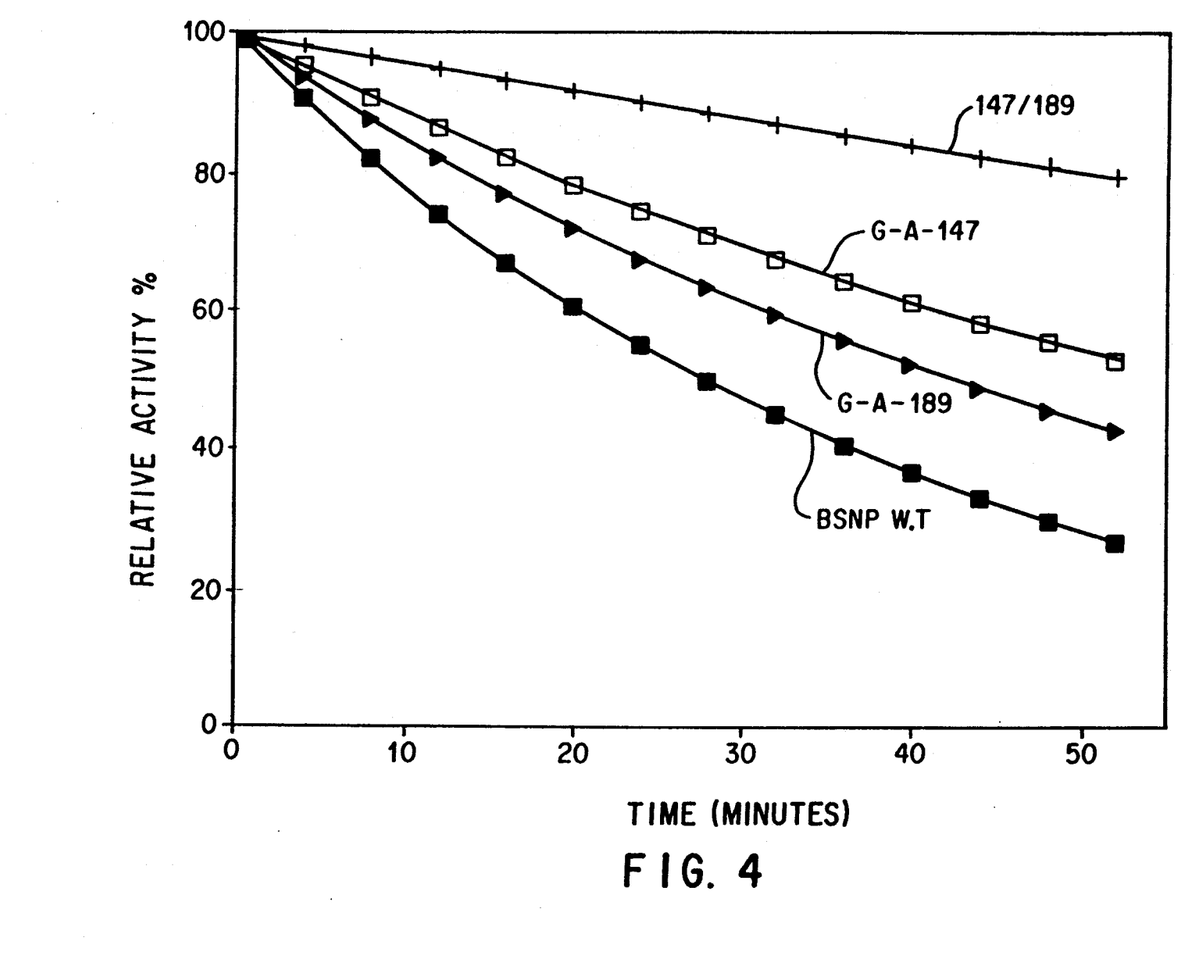
FIGS. 4, 5 and 6: show the curves of the thermal denaturing of wild-type neutral protease and of the 147, 189 and 147/189 mutants at 55° C., 58° C. and 61° C., expressed as the % of activity remaining in relation to the preincubation time.
Figure 5:
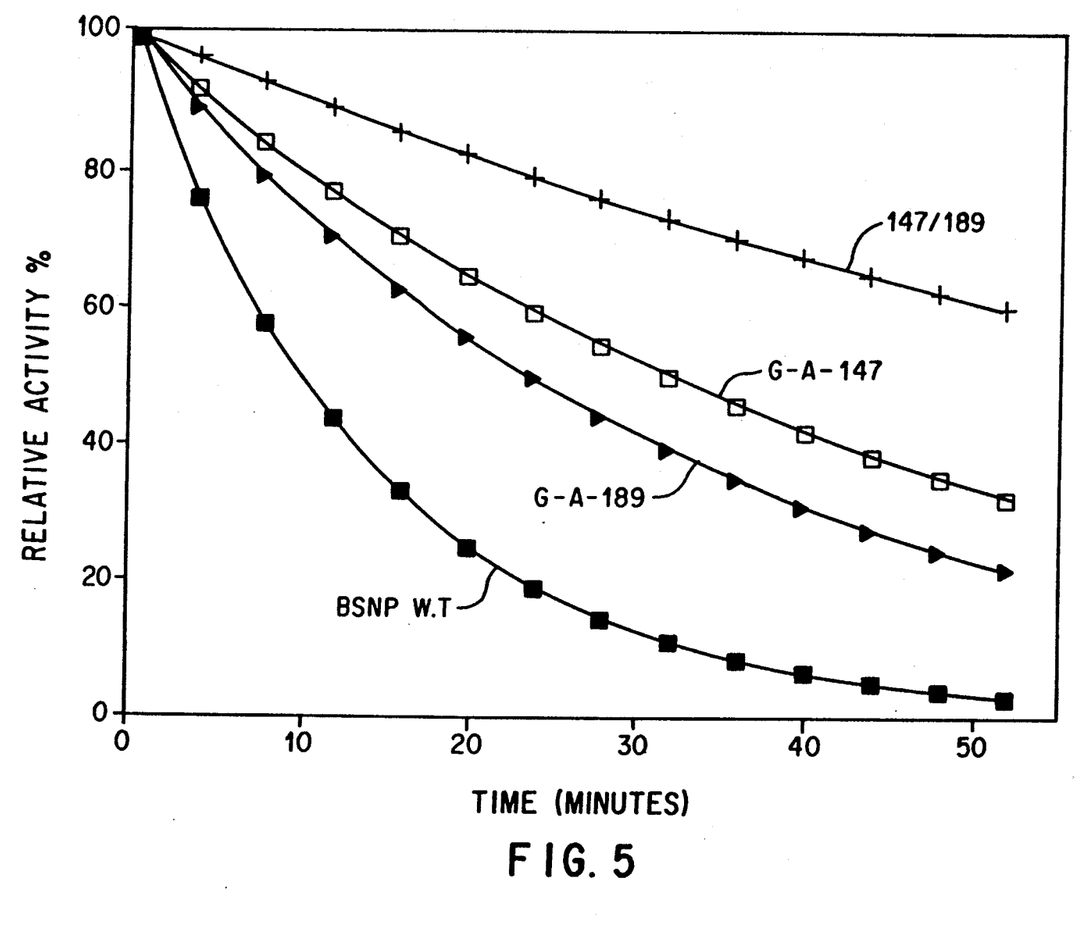
Figure 6:
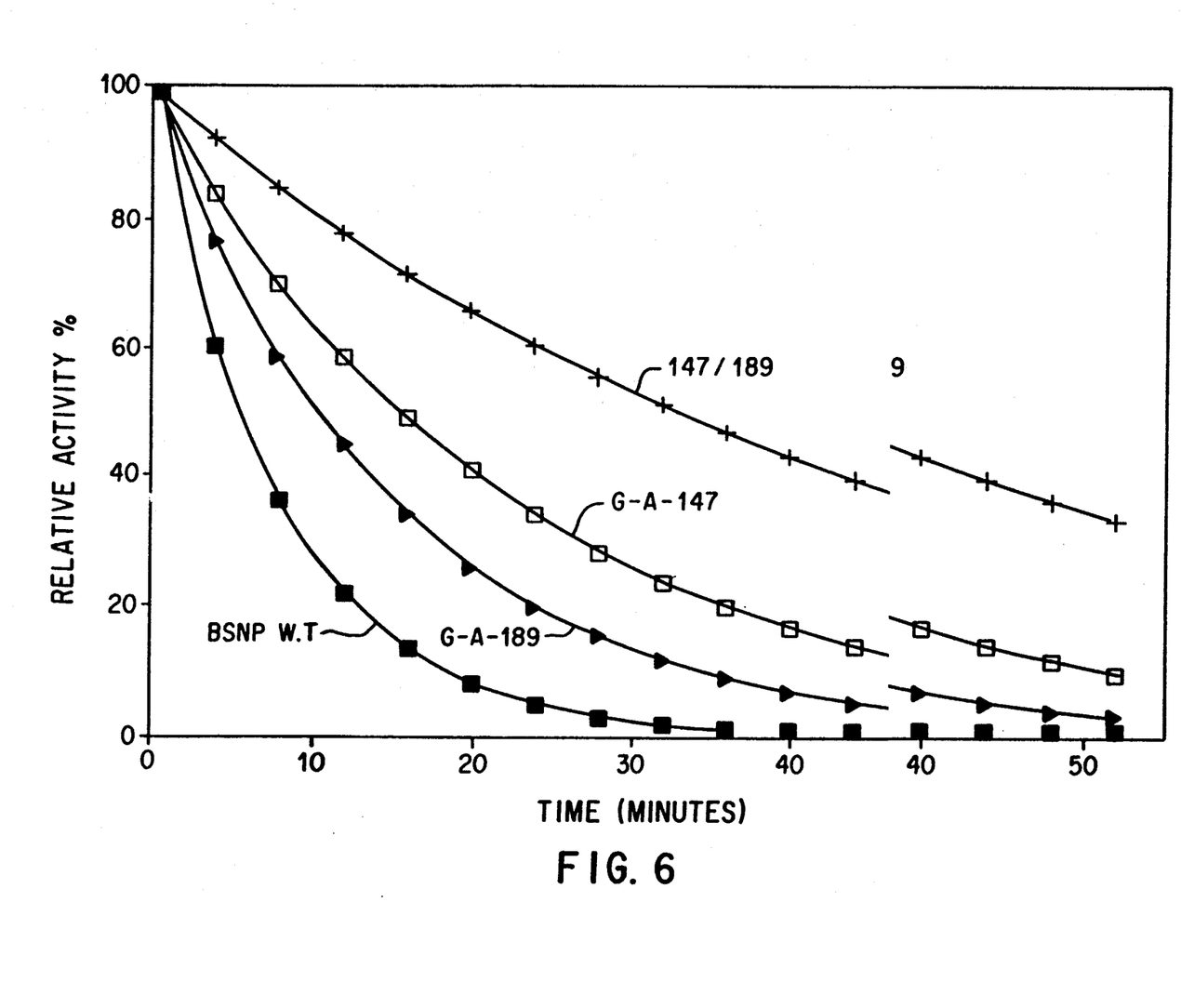

FIGS. 4, 5 and 6 show the losses of activity of the mutated proteases and of the wild-type protease at 55° C., 58° C. and 61° C.

The times taken to halve the enzymatic activities at these temperatures were:

TABLE III

|  | 55° C. | 58° C. | 61° C. |
| --- | --- | --- | --- |
| wild-type PN | 27 | 11 | 5 |
| 147 | 59 | 31 | 15 |
| 189 | 44 | 24 | 10.5 |
| 147/189 | 169 | 70 | 33 |

It can be seen from the table above that the average life of 147 is 3 times as long as that of wild-type PN, and that of 189 is about twice as long, whilst that of the double mutant is 7 times as long.

These results show clearly that the simultaneous replacement of the glycine aminoacid with alanine in positions 147 and 189 considerably increases the ther-

TABLE 1

| Substrate | Isocratic programme % B | enzyme concentration μg/ml | withdrawal times sec. | substrate concentration mM | R.T. prod. min. | R.T. substr. min. |
| --- | --- | --- | --- | --- | --- | --- |
| Z—Phe—Leu—Ala | 36 | 0.04 | 30 | 0.2 . . . 5 | 6.9 | 10 |
| Z—Ala—Leu—Ala | 23 | 0.05 | 30 | 1 . . . 20 | 4.8 | 11.7 |
| Z—Gly—Leu—Ala | 23 | 0.15 | 60 | 1 . . . 20 | 4 | 13.1 |
| Z—Val—Leu—Ala | 30 | 5 | 120 | 0.5 . . . 10 | 4.9 | 7.2 |

TABLE 2

|  | Z—Phe—Leu—Ala | Z—Ala—Leu—Ala | Z—Gly—Leu—Ala | Z—Val—Leu—Ala |  |
| --- | --- | --- | --- | --- | --- |
| PN w.t. | 1.42 | 11.42 | 21.29 | 2.84 | Km |
|  | 1986 | 3005 | 1150 | 6.12 | Kcat |
|  | 1398.59 | 263.13 | 54.01 | 2.15 | Km/Kcat |
| 147 | 9.36 | c.a. 202 | 35.27 | 24 | Km |
|  | 1933 | c.a. 3500 | 105.8 | 3.76 | Kcat |
|  | 206.52 |  | 3 | 0.16 | Km/Kcat |
| 189 | 2.53 | 1.53 | 2.38 | 0.96 | Km |
|  | 2139 | 2694 | 1847 | 13.12 | Kcat |
|  | 845.45 | 1760.78 | 776.05 | 13.6 | Km/Kcat |
| 147/189 | 0.95 | 8.72 | 4.39 | 6.97 | Km |
|  | 1038 | 1329 | 186.4 | 7.61 | Kcat |
|  | 1084.64 | 152.41 | 42.5 | 1.091 | Km/Kcat |

EXAMPLE 5

The kinetics of the thermal inactivation

Thermal inactivation studies were carried out by the incubation of solutions of wild-type neutral protease, mal stability of the protease without affecting its enzymatic activity.

We claim:

1. A substantially pure mutant neutral protease, wherein said mutant neutral protease is a mutant of wild-type neutral protease which is endogenous to *Bacillus subtilis*, wherein said mutant neutral protease retains enzymatic activity at temperature at which said wild-type neutral protease becomes inactive, wherein in said mutant neutral protease, at least one of the amino acid residues Gly 189 and Gly 147 of the amino acid sequence of said wild-type neutral protease each is replaced by Ala.

2. The mutant neutral protease of claim 1, wherein Gly 189 of said wild-type neutral protease is replaced by L-alanine.

3. The mutant neutral protease of claim 1, wherein Gly 189 and Gly 147 of said wild-type neutral protease each is replaced by L-alanine.

4. The mutant neutral protease of claim 1, produced by a method comprising:

(a) growing a strain of *Bacillus Subtilis* transformed with an expression plasmid comprising a mutagenized gene of wild-type neutral protease which encodes a mutant of wild-type neutral protease; a marker for the selection of transformants; and a replicon which enables replication of said plasmid in *Bacillus subtilis*, in a suitable culture medium containing sources of carbon, nitrogen and mineral salts;

(b) separating said *Bacillus subtilis* from said medium; and (c) purifying from said medium said mutant neutral protease thus obtained.

5. The mutant neutral protease of claim 4, wherein said *Bacillus subtilis* is *Bacillus subtilis* SMS 108 (pSM 375) CBS 640.89.

6. The mutant neutral protease of claim 4, wherein said *Bacillus subtilis* is *Bacillus subtilis* SMS 108 (pSM 376) CBS 641.89

* * * * *

SEQUENCE LISTING ( 1 ) GENERAL INFORMATION:

-continued (i i i) NUMBER OF SEQUENCES: 3

(2) INFORMATION FOR SEQ ID NO: 1:

(i) SEQUENCE CHARACTERISTICS:
        (A) LENGTH: 33 base pairs
        (B) TYPE: nucleic acid
        (C) STRANDEDNESS: single
        (D) TOPOLOGY: linear     (i i) MOLECULE TYPE: DNA     (x i) SEQUENCE DESCRIPTION: SEQ ID NO: 1:

GAAGACTGGG ATATCGCAGA AGACATTACG GTC     33

(2) INFORMATION FOR SEQ ID NO: 2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear     (i i) MOLECULE TYPE: DNA     (x i) SEQUENCE DESCRIPTION: SEQ ID NO: 2:

CATGAAATGA CGCATGCAGT CACCCAAGAA ACA     33

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (i i) MOLECULE TYPE: DNA     (x i) SEQUENCE DESCRIPTION: SEQ ID NO: 3:

GGTTCATTCT TCTCTCCG     18